(12) United States Patent
Poulin

(10) Patent No.: US 12,268,490 B2
(45) Date of Patent: Apr. 8, 2025

(54) MAGNETIC RESONANCE IMAGING DEVICES, METHODS, AND SYSTEMS FOR VASCULAR INTERVENTIONS

(71) Applicant: Nathan Poulin, San Francisco, CA (US)

(72) Inventor: Nathan Poulin, San Francisco, CA (US)

( * ) Notice: Subject to any disclaimer, the term of this patent is extended or adjusted under 35 U.S.C. 154(b) by 193 days.

(21) Appl. No.: 16/706,325

(22) Filed: Dec. 6, 2019

(65) Prior Publication Data
US 2020/0113480 A1    Apr. 16, 2020

Related U.S. Application Data

(63) Continuation of application No. PCT/US2018/036717, filed on Jun. 8, 2018.

(60) Provisional application No. 62/628,938, filed on Feb. 10, 2018, provisional application No. 62/517,175, filed on Jun. 9, 2017.

(51) Int. Cl.
| | |
|---|---|
| *A61B 5/06* | (2006.01) |
| *A61B 5/055* | (2006.01) |
| *A61B 18/00* | (2006.01) |
| *A61B 18/14* | (2006.01) |

(52) U.S. Cl.
CPC .............. *A61B 5/062* (2013.01); *A61B 5/055* (2013.01); *A61B 18/1492* (2013.01); *A61B 2018/00577* (2013.01)

(58) Field of Classification Search
CPC ................ A61B 18/1492; A61B 18/18; A61B 2018/00577; A61B 2034/2051; A61B 2090/306; A61B 2090/374; A61B 34/20; A61B 5/055; A61B 5/062; A61B 90/37
See application file for complete search history.

(56) References Cited

U.S. PATENT DOCUMENTS

4,582,057 A * 4/1986 Auth .................... A61B 18/082
219/241
5,928,145 A * 7/1999 Ocali ............... G01R 33/34084
324/309

(Continued)

FOREIGN PATENT DOCUMENTS

| WO | WO-01/73461 A2 | 10/2001 |
|---|---|---|
| WO | 2018/227126 A1 | 12/2018 |

OTHER PUBLICATIONS

Extended European Search Report for EP Application No. 18813022.3 dated Jun. 11, 2021.
International Search Report and Written Opinion for International Application No. PCT/US2018/036717 dated Sep. 13, 2018.
Kocaturk et al., "Active Two-Channel 0.035" Guidewire for Interventional Cardiovascular MRI, Journal of Magnetic Resonance Imaging, 30:461-465 (2009).

(Continued)

*Primary Examiner* — Chao Sheng
*Assistant Examiner* — Maria Christina Talty
(74) *Attorney, Agent, or Firm* — Foley Hoag LLP; Lucas P. Watkins; Joshua S. Matloff

(57) ABSTRACT

The present disclosure provides a system for localizing the position of an endovascular probe and collecting high-resolution images of the anatomy surrounding the probe. In particular, a switchable endovascular imaging antenna/probe and related devices are disclosed, which are conveniently switchable between a configuration that allows the localization with high precision of the distal tip of an endovascular probe, and another configuration that allows imaging in the locality of the probe tip. Embodiments are also disclosed capable of delivering ablation therapy.

20 Claims, 10 Drawing Sheets

(56) References Cited

U.S. PATENT DOCUMENTS

| | | | |
|---|---|---|---|
| 6,246,896 B1* | 6/2001 | Dumoulin | A61B 18/1492 606/34 |
| 6,453,189 B1* | 9/2002 | Gilderdale | G01R 33/34084 600/423 |
| 7,270,656 B2 | 9/2007 | Gowda et al. | |
| 8,457,712 B2* | 6/2013 | Unal | G01R 33/286 600/407 |
| 2007/0191829 A1 | 8/2007 | McGee | A61B 18/14 606/41 |
| 2008/0208034 A1 | 8/2008 | Yang et al. | |
| 2008/0208039 A1* | 8/2008 | Kurpad | A61B 90/36 600/424 |
| 2010/0317961 A1 | 12/2010 | Jenkins et al. | |
| 2011/0077638 A1* | 3/2011 | Brannan | A61B 90/06 606/33 |
| 2012/0123406 A1* | 5/2012 | Edmunds | A61B 18/1482 606/41 |
| 2013/0123598 A1* | 5/2013 | Jenkins | A61B 34/20 600/374 |
| 2013/0274591 A1* | 10/2013 | Sonmez | G01R 33/287 600/411 |
| 2014/0094792 A1* | 4/2014 | Sharonov | A61B 18/1233 606/34 |
| 2017/0143234 A1 | 5/2017 | Degertekin et al. | |

OTHER PUBLICATIONS

Qiu et al., "Development of a 0.014-inch Magnetic Resonance Imaging Guidewire," Mag Res Med 53:986-990 (2005).

"Transmission Line" https://en.wikipedia.org/wiki/Transmission_line, Last edited Dec. 13, 2023, Accessed Feb. 5, 2024.

Vernickel et al., "A safe transmission line for MRI." IEEE transactions on biomedical engineering 52.6 (2005): 1094-1102.

Atalar et al., "High resolution intravascular MRI and MRS by using a catheter receiver coil," Magnetic Resonance in Medicine 36.4 (1996): 596-605.

El-Sharkawy et al., "The performance of interventional loopless MRI antennae at higher magnetic field strengths," Medical Physics 35.5 (2008): 1995-2006.

Sathyanarayana et al., "MRI endoscopy using intrinsically localized probes." Medical Physics 36(3) (2009): 908-919.

Sathyanarayana et al., "Towards Real-Time Intravascular Endoscopic Magnetic Resonance Imaging," JACC: Cardiovascular Imaging 3.11 (2010): 1158-1165.

Özen et al., "Safety of active catheters in MRI: termination impedance versus RF-induced heating", Magnetic Resonance in Medicine 81(2): 1412-1423 (2019).

* cited by examiner

MAGNETIC RESONANCE IMAGING DEVICES, METHODS, AND SYSTEMS FOR VASCULAR INTERVENTIONS

CROSS REFERENCE TO RELATED APPLICATIONS

This application is a continuation of International Application No. PCT/US2018/036717, filed Jun. 8, 2018, which claims the benefit of Provisional Application No. 62/628,938 filed Feb. 10, 2018 and Provisional Application No. 62/517,175, filed Jun. 9, 2017, each of which is hereby incorporated by reference herein in its entirety.

FIELD OF THE DISCLOSED SUBJECT MATTER

The disclosed subject matter relates to a system for localizing the position of an endovascular probe. In particular, the present disclosed subject matter is directed to a switchable endovascular imaging, radiofrequency probe and related devices, which in one configuration allows the localization with high precision of the distal tip of the endovascular probe, and in another configuration allows imaging in the locality of the probe. In one or more configurations of the disclosed subject matter, ablation therapy may be delivered.

DESCRIPTION OF RELATED ART

A variety of methods and systems are known for imaging during interventional procedures. Traditionally, endovascular procedures have relied on X-ray fluoroscopy to guide the navigation of catheters and associated therapeutic devices through vascular routes. Such conventional methods and systems generally have been considered satisfactory for their intended purpose. Recently, however, the range of percutaneous procedures has increased, and some procedures currently in use require long fluoro times, which exposes the patient to a continuous dose of ionizing radiation as well as intra-arterial injection of nephrotoxic, iodinated contrast agent. In addition to these direct safety concerns, X-ray angiograms are mostly restricted to the vessel lumen and the X-ray projections introduce image artifacts.

Magnetic resonance imaging (MRI) is useful for providing detailed 3D soft tissue contrast which is, in many cases, superior to other imaging modalities. The additional information provided by MRI has the potential to transform the way interventional treatments are practiced. The images made available by MRI techniques could not only improve the outcomes of current procedures but could expand the scope of treatment options, since physicians would be able to see the anatomy that they are directly working on.

But when used as a diagnostic tool, conventional MR image acquisitions use imaging coils placed external to the patient. These conventional methods are not well-suited for certain anatomy. Deep arteries, such as the coronaries, renal arteries, and peripheral arteries, are poorly seen using external imaging coils. Better techniques for characterizing plaque content in these areas, in vivo, are needed.

Thus there remains a need for an efficient and economic method, device, and system for navigating under MRI guidance to deep and narrow vasculature. The field also lacks a probe that seamlessly integrates device tracking, imaging, and ablation without introducing excessive bulk, compromising function, or introducing uncontrollable RF heating hazards.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

The disclosed subject matter also includes a system for tracking the tip of an endovascular probe and collecting images of the surrounding anatomy. In certain embodiments, the present disclosure provides an endovascular probe, comprising a conductor; a tracking coil with a first end and a second end; and a switchable coupling mechanically coupled to the conductor and the first end of the tracking coil. In certain embodiments, when the switchable coupling is in a first configuration, the conductor is in electrical contact with the first end of the tracking coil; and when the switchable coupling is in a second configuration, the conductor is not in electrical contact with the first end of the tracking coil.

In certain embodiments, the switchable coupling comprises a photoresponsive material (e.g., a thermoactive material) mechanically coupled to the conductor and the tracking coil; and an optical fiber in optical communication with the switching material. In certain such embodiments, the endovascular probe further comprises a light source (e.g., a laser) in optical communication with the optical fiber. In certain such embodiments, the switchable coupling further comprises a membrane enclosing the switching material. In certain such embodiments, the photoresponsive material (e.g., the thermoactive material) has a positive coefficient of thermal expansion; when the photoresponsive material (e.g., the thermoactive material) is at a first temperature, the switchable coupling is in the first configuration; and when the switching material is at a second temperature that is higher than the first temperature, the switchable coupling is in the second configuration. In other such embodiments, the photoresponsive material (e.g., the thermoactive material) erial has a negative coefficient of thermal expansion; when the switching material is at a first temperature, the switchable coupling is in the second configuration; and when the switching material is at a second temperature that is higher than the first temperature, the switchable coupling is in the first configuration.

In certain embodiments, the switchable coupling comprises a mechanical switching device mechanically coupled to the radiofrequency tracking coil; and a wire mechanically coupled to the mechanical switching device. In certain such embodiments, the switching device comprises a hinge, which may be bistable.

In certain embodiments, the endovascular probe further comprises a second conductor in electrical contact with the second end of the tracking coil.

In certain embodiments, the endovascular probe further comprises a second conductor and a second switchable coupling mechanically coupled to the second conductor and the second end of the tracking coil. In certain such embodiments, the second switchable coupling comprises a second photoresponsive material (e.g., a second thermoactive material) mechanically coupled to the second conductor and the second end of the tracking coil; and a second optical fiber in optical communication with the switching material.

In certain embodiments, the endovascular probe further comprises a second light source (e.g., a second laser) in optical communication with the second optical fiber. In certain embodiments, the second switchable coupling further comprises a membrane enclosing the switching material.

To achieve these and other advantages and in accordance with the purpose of the disclosed subject matter, as embodied and broadly described, the disclosed subject matter includes a method of operating an intravascular probe, comprising inserting the endovascular probe of any one of claims 1-15 into a blood vessel; tracking the position of the the tip of the endovascular probe in the blood vessel; and collecting an image of the anatomy surrounding the tip of the endovascular probe.

In certain embodiments, tracking the position of the tip of the endovascular probe comprises placing the endovascular probe in the first configuration and applying a tracking pulse sequence to the tracking coil or an external coil. In certain embodiments, collecting an image comprises placing the endovascular probe in the second configuration and applying an imaging pulse sequence to the tracking coil or an external coil.

In certain embodiments, the disclosed methods further comprise placing the endovascular probe in an ablation configuration and applying an ablation pulse sequence to an external coil.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION OF EXEMPLARY EMBODIMENTS

Figure 1:
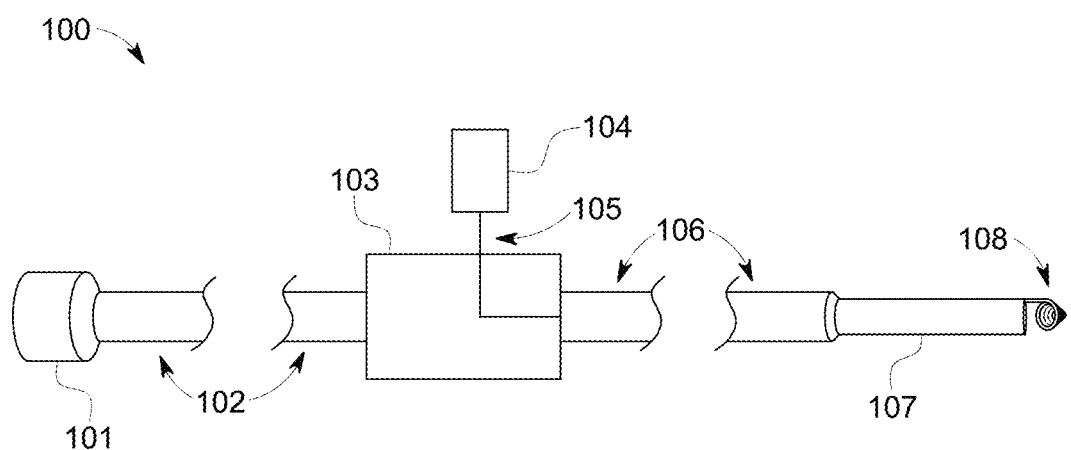
FIG. 1 is a schematic representation of an embodiment of an endovascular probe system in accordance with the disclosed subject matter.

Endovascular RF probes have been used as internal receiving coils for techniques using MRI. These internal coils provide an enhanced signal due to their proximity to the imaging volume, as well as a reduced body noise factor because of a smaller imaging coverage when compared with external coils. Thus, higher resolution images can be obtained in a shorter period of time. However, endovascular RF probes are limited by numerous design challenges that preclude clinical feasibility. For example, looped endovascular coils provide a high SNR but have a quickly vanishing imaging coverage (Sathyanarayana, Shashank, and Paul A. Bottomley. *Medical physics*. 36.3 (2009):908-919) and are bulky. Reducing the coil diameter of these probes to access narrow vasculature further compromises imaging coverage. Multimode probes that include both active tracking and imaging capabilities often contain many lumped elements or large solenoids (Hillenbrand, Claudia M, et al. Magnetic resonance in medicine 51.4 (2004): 668-675), and lack suitable functional integration. There are examples of probes where imaging and visualization or active tracking functions are mediated by different components of the probe, and where these components can be turned 'off' by detuning of one component of the circuit. One example (Weiss, Steffen, et al. *Magnetic resonance in medicine* 52.4 (2004): 860-868.) consists of a probe with a laser activated optical fiber, fed to a photodiode at the tip of a catheter. The photodiode is in parallel to a resonant circuit, which consists of two capacitors and an inductor. When the photodiode is illuminated, its impedance changes, effectively detuning the resonant circuit and thereby turning the circuit off. A similar probe incorporates imaging as well (Zuehlsdorff, Sven, et al. *Magnetic resonance in medicine* 52.1 (2004): 214-218). Another related example (Fandrey, Stephan, Steffen Weiss, and *Jörg Müller*. 67.1 (2012): 148-155) comprises a probe used as a receiver for imaging, and the circuit can be detuned using an optical fiber similar to Weiss et al. (*MRM*, 2004). However, they use a second optical fiber and a modulator to convert the RF signal used for imaging into an optical signal. The disadvantage of all of these probes is that they use many circuit and/or optical components, some of which are situated in the vascular space.

The simplest RF probe for vascular entry is the loopless antenna (or imaging guidewire) (Ocali. and Ogan, amd Ergin Atalar, *Magnetic resonance in medicine* 37.1 (1997): 112-118.). This probe can be thought of as a dipole, with one pole being the quarter-wavelength extension of the inner conductor, which is the guidewire (primary imaging component) and the other pole being the shield of the coaxial cable. Its imaging performance has been studied extensively, and it has an elevated SNR at its proximal end in a cylindrical volume, which extends partially into the shielded cable. Such probes have been navigated through the vasculature of animal models, but their use as receiving probes for imaging of blood vessels in living humans has only been adequately explored in a single study (Larose, Eric, et al. *Circulation* 112.15 (2005): 2324-2331.), where the antenna was slipped into the superficially located common iliac artery of 25 patients with atherosclerotic lesions. It was shown that the loopless antenna could obtain suitable images for delineation of plaque composition. This intravascular MRI antenna is better at resolving certain plaque characteristics, such as calcification, lipid content, and plaque borders, and allowed for better diagnosis of vessel wall disease when compared with surface coils and intravascular ultrasound (IVUS).

However, dipole antennas such as these have significant drawbacks. Their diffuse and diminishing sensitivity profiles towards their distal ends make it difficult or impossible to safely localize these antenna tips with high enough frame rates for guidance to distant located target locations. Adding tapered insulation to the antenna (Qian, Di, et al. *Magnetic resonance in medicine* 63.3 (2010): 797-802.) can extend the imaging performance of the distal section, but this is not an adequate solution for actively tracking (Dumoulin, Charles, et al. *Magnetic resonance in medicine* 29.3 (1993): 411-415) the precise tip location. Placing a tightly wound solenoid in an open circuit configuration (or grounded by conductive medium, instead of being shorted by the coaxial shield) at the distal tip of the antenna can increase tip visibility (Sonmez, Merdim, et at. *Journal of Cardiovascular Magnetic Resonance* 14.1 (2012): 38.), but this impairs the imaging performance of the probe.

Precise localization of the distal antenna tip or distal tip of any other endovascular probe, combined with the acquisition of detailed background anatomical images during real-time magnetic resonance guidance, is essential if one hopes to navigate these probes to distant, delicate, and tortuous vasculature. However, achieving precise localization at a sufficient framerate, in a probe that also has the ability to acquire therapeutically useful images, has not yet been achieved, due to constraints of vascular anatomy and limitations of probe design.

There has been a significant amount of development in the manipulation of the configuration of materials. Mechanical deformation of materials in a precisely controlled manner can provide unintuitive improvements to devices and machines. A class of engineered materials is capable of exhibiting shape responsive behavior, and an emerging subset of these use light as the activating source for mechanical work. These include polymeric and carbonaceous materials, molecular crystals, and photostrictive ceramics. Two broad pathways for light-induced shape change are photothermal and photochemical stimuli. Photothermal mechanisms include order-disorder transitions, swelling, and simple coefficient of thermal expansion. Photochemical mechanisms primarily consist of trans-cis isomerization, especially of azobenzene, but ring-opening of chromophores, as well as dissociation reactions, are additional mechanisms.

In fact, many of these light responsive materials are particularly advantageous because the shape change they undergo is reversible and repeatable—light stimulation induces a mechanical change in the material, such as twisting, bending, or expansion/contraction and when the light source is removed, the material reverts to its original shape. This is in contrast to other shape-shifting materials, such as the majority of shape memory polymers that undergo irreversible shape change in which they store a metastable shape and return to a more stable shape given the proper stimulus. But photomechanical materials are also beneficial, when compared with other mechanical deformation pathways because they may be actuated wirelessly and without contact (Ware, Taylor H., *Photomechanical Materials, Composites, and Systems: Wireless Transduction of Light into Work* (2017); 327-368.).

Any application which uses intravascular ultrasound (IVUS) could benefit from using intravascular MRI since it offers superior soft tissue contrast and easily interpreted images with respect to IVUS. Plaque assessment prior to angioplasty or stenting for coronary (chronic total occlusions) and peripheral arterial disease, is presently the main use of IVUS. But beyond assessment of plaque vulnerability, plaque erosion perhaps will be another important application of intravascular MRI. Neurointerventions may be feasible as well. In cases where patients receive endovascular therapy for treatment of ischemic stroke, X-ray angiography is typically used to verify reperfusion and to rule out hemorrhage, post-thrombolysis or mechanical thrombectomy. It would be beneficial to assess tissue damage at the core infarct, post-treatment, with intravascular MRI. And since vascular access would already have been obtained, it would be safe and easy to continue with guidance under MRI. Additionally, there are many other conditions with other anatomies where treatment protocols are limited by the use of X-ray angiography, external MR-imaging coils, and other imaging modalities. Ablation via vascular access under MRI guidance for renal denervation or in narrow vasculature, potentially for vascular tumors and other conditions, as opposed to the open chambers and large vessels for arrhythmia ablations, is attractive and would be another feature which would open up the possibilities for intravascular MRI.

Reference will now be made in detail to exemplary embodiments of the disclosed subject matter, an example of which is illustrated in the accompanying drawings. The method and corresponding steps of the disclosed subject matter will be described in conjunction with the detailed description of the system.

The methods and systems presented herein may be used for guiding intravascular probes and collecting MRI images from their vicinities. The disclosed subject matter is particularly suited for guiding a probe through vasculature in a guiding configuration, then imaging surrounding tissue at a target site in an imaging configuration. For purposes of explanation and illustration, and not limitation, an exemplary embodiment of the system in accordance with the disclosed subject matter is shown in FIG. 1 and is designated generally by reference character 100. Similar reference numerals (differentiated by the leading numeral) may be provided among the various views and Figures presented herein to denote functionally corresponding, but not necessarily identical structures.

As shown in FIG. 1, the system 100 generally includes an antenna (107), a radiofrequency tracking coil (108), and a switchable coupling (not shown in FIG. 1, see FIG. 2 and others). The system generally further includes components useful for connecting the system to an MRI scanner. As shown in FIG. 1, the system may include a bnc connector or other suitable connecting component (101), which connects to a coaxial cable (102), which in turn connects to a tuning/matching/decoupling box which could also include a balun (103). The bnc (101), connects to the MRI scanner. On the other end of 103, another coaxial cable, 106, is connected, which connects with the antenna, 107. The antenna, 107, may comprise the stripped inner conductor of 106, or may comprise any other MR compatible conductive material. What is called an antenna, 107, could also be any coil design suitable for imaging, comprising conductors, optionally comprising lumped elements such as capacitors, inductors, and/or thin film fabricated structures. In certain preferred embodiments, a laser, 104, feeds an optical fiber, 105. The optical fiber, 105, can enter at 103 or any other suitable location in the system and can be fed through 106 and through the center of 107, where it meets the switchable coupling (containing, e.g., a thermally or photo-active material) at the distal tip of 107. An inductive tracking loop, 108, is mounted on the switchable coupling at the distal tip of 107.

The active tracking loop, 108, shown in FIG. 1, may be of any suitable shape known in the art and may comprise any suitable number of loop turns (e.g., 1 turn, 2 turns, 3 turns, or more). The loop may contain an open axis, free of any catheter, antenna, or MR inactive material, so that a signal peak can be generated, which localizes the position of the distal tip of the device. If a portion of the loop, 108, is oriented in the XY plane, where Z is the direction of the bore of the MRI scanner, then the section of the loop, 108, closest to the antenna generates an electric field which cancels the electric field produced by the distal end of the shaft of the antenna, 107. This creates an electric void in the axis of the inductive loop, 108, which allows for MRI signals to be generated. As mentioned, the active loop, 108, can be any suitable active tracking component, such as a solenoid wrapped around the distal shaft of 107, with a solder joint at the distal most tip of 107, leaving the probe as an open circuit. This design is shown in FIG. 3.

A cross-section of an embodiment of the present invention can be seen in FIG. 2, which shows a close up view of the probe tip, 200. As mentioned above, the antenna, 207, may comprise any conductive, MR compatible material. Antenna 207 may further comprise an outer insulation, which is not shown in any of the figures. An optical fiber, 209, perhaps comprising only the core and a cladding, can be situated within the center axis of the antenna, 207. The optical fiber, 209, is coupled (e.g., optically coupled) to a switchable coupling, i.e. a coupling that comprises a non-conductive material capable of expansion or contraction, or other shape change, upon application of a suitable stimulus (e.g., a thermally active or photoactive material), 210, such that light transmitted through the optical fiber illuminates the material and can induce the desired shape change (e.g., expansion or contraction). The shape change may be along a preferred direction, such as along the axis of the probe so as to axially displace the distal portion of the antenna (e.g., the conductive active tracking loop). Alternatively, the shape change may be in a direction perpendicular to the axis of the probe so as to laterally displace the distal portion of the antenna. The conductive active tracking loop, 208, is mounted on 210, and makes contact with the conductive antenna, 207. See Susil, Robert C., et al. *Magnetic Resonance in Medicine* 50 (2003): 383-390 for a similar probe design. The thermally active material, 210, can consist of a paraffin wax based material, gel, hydrogel, polymer, shape memory polymer or alloy, liquid crystal elastomer, or any other material which expands and/or contracts when heated. The thermally active material, 210, may be encapsulated or surrounded by a diaphragm layer, which is not shown. A diaphragm or insulating material is needed if the thermal material, 210, changes phase. In other words, if the thermally active material, 210, turns into a liquid when heated, or if it changes viscosity in any significant way, then the diaphragm layer prevents leakage of the material. Preferably the thermally active or photoactive material, 210, does not substantially conduct electricity so that it does not interfere with the operation of the antenna.

In any embodiment which uses a photoresponsive switch (e.g., embodiments based on thermoactive or photoactive materials), an appropriate laser or other light source may be used to illuminate the optical fiber. The laser may be positioned outside of the scanner and coupled to the optical fiber. The optical fiber may exit the probe from a plurality of positions along the proximal portion of the probe. The most important aspect of the laser is its ability to transfer energy to the switchable coupling (e.g., the thermally responsive, or photoactive material). The laser may be a small, battery powered source, which can be easily exchanged for another source if needed.

Figure 2A:
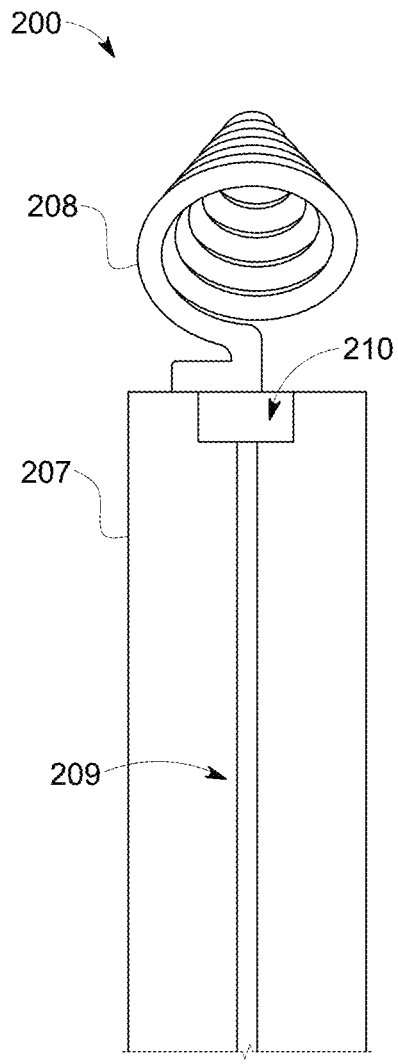
FIGS. 2A and 2B are schematic representations of two configurations of an embodiment of an endovascular probe system in accordance with the disclosed subject matter.
Figure 2B:
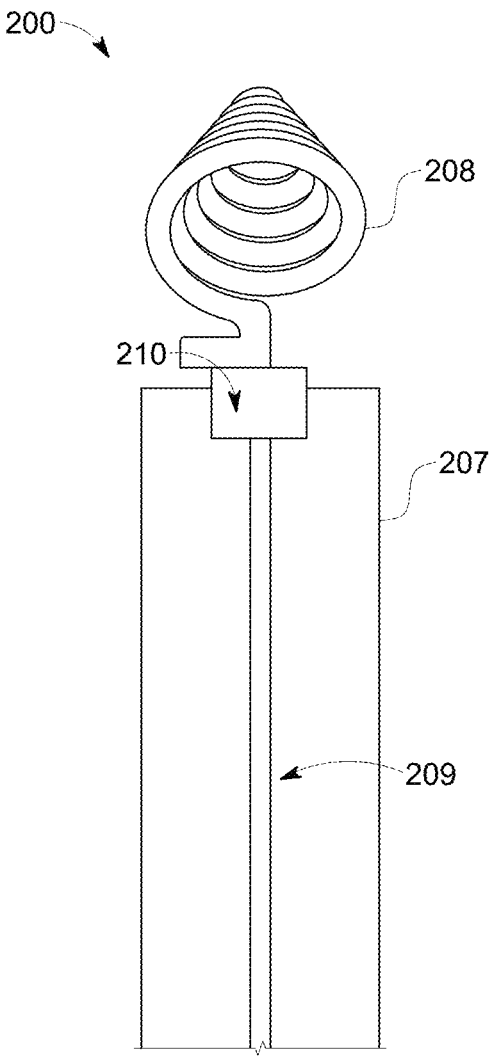

The embodiment of FIG. 2 may exist in two configurations. In the first configuration, FIG. 2A, the thermally active or photoactive material, 210, is in its unexpanded state, and the active tracking loop, 208, is electrically coupled to the base of the antenna, 207. In this configuration, the tracking loop, 208, is part of the overall circuit and may be used to track the tip of the probe. In the second configuration, FIG. 2B, the thermally active or photoactive material, 210, is in its expanded state, and the tracking loop, 208, is not electrically coupled to the base of the antenna, 207. The direction in which the tracking loop is displaced is unimportant to this feature, so long as the tracking loop is no longer electrically coupled to the base of the antenna. In this configuration, FIG. 2B, 208 is no longer part of the circuit. Even if alternating current is present on 207, 208 will not inductively couple with 207, because 208 has a resonant frequency which is very different from the resonant frequency of 207. Thus, the tracking loop is effectively toggled 'off', FIG. 2B.

In embodiments where the thermally active or photoactive material, 210, comprises a material with a positive thermal expansion coefficient, sufficient irradiation of 210 with laser energy coupled to an optical fiber (core and cladding), 209, will cause 210 to expand. By expanding, the thermally active material, 210, lifts the tracking loop, 208, from the base of the antenna, 107. When laser irradiation is discontinued, the thermally active or photoactive material returns to its unexpanded state, and the electrical coupling between the antenna and the tracking loop is restored.

In embodiments where 210 comprises a material with a negative thermal expansion coefficient, the absence of irradiation from a laser causes the thermally active or photoactive material to be in an expanded state, with the result that the tracking loop is electrically decoupled from the antenna. Irradiation with laser light causes the thermally or photoactive material to contract, thereby causing the tracking loop to become electrically coupled with the antenna.

Figure 3A:
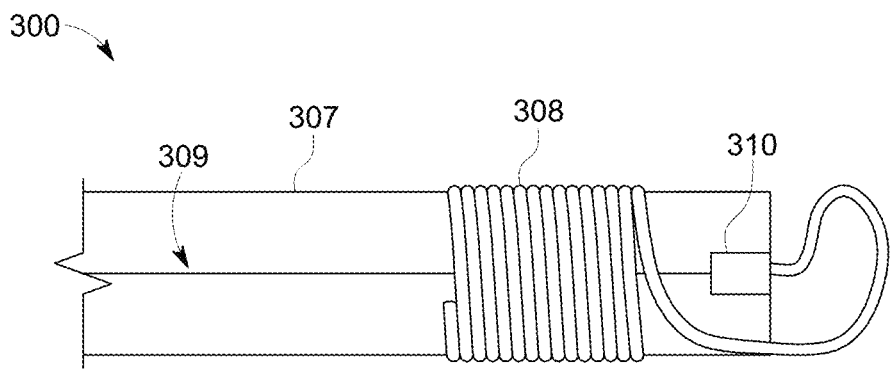
FIGS. 3A and 3B are schematic representations of two configurations of an embodiment of an endovascular probe system in accordance with the disclosed subject matter.
Figure 3B:
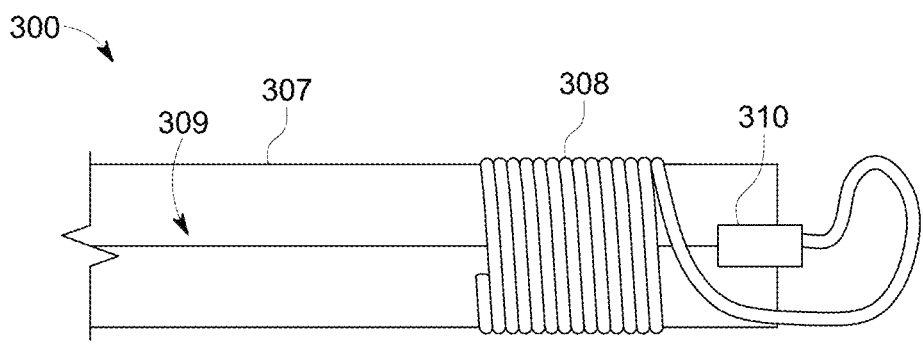

A similar embodiment to FIG. 2 of probe tip 300 is depicted in FIG. 3. In this embodiment, the tracking coil, 308, consists of a wire wrapped in a solenoid around the distal tip of the antenna, 307. This configuration of 308 is similar to that in Sonmez, Merdim, et al. Journal of cardiovascular Magnetic Resonance 14.1 (2012): 38. One end of 308 is connected to the photoactive material, 310, and the other end of 308 is not electrically connected to any other conductor. In FIG. 3A, the end of 308 connected to the photoactive material, 310, is also electrically connected to 307. In the configuration shown in FIG. 3B, the end of 308 connected to 310 is no longer electrically connected to 307. An optical fiber, 309, perhaps comprising only the core and a cladding, can be situated within the center axis of the antenna, 307. The optical fiber, 309, is coupled (e.g., optically coupled) to a switchable coupling, i.e. a coupling that comprises a non-conductive material capable of expansion or contraction, or other shape change (e.g., a thermally active or photoactive material), upon application of a suitable stimulus, 310 such that light transmitted through the optical fiber illuminates the material and can induce the desired shape change (e.g., expansion or contraction).

Figure 4A:
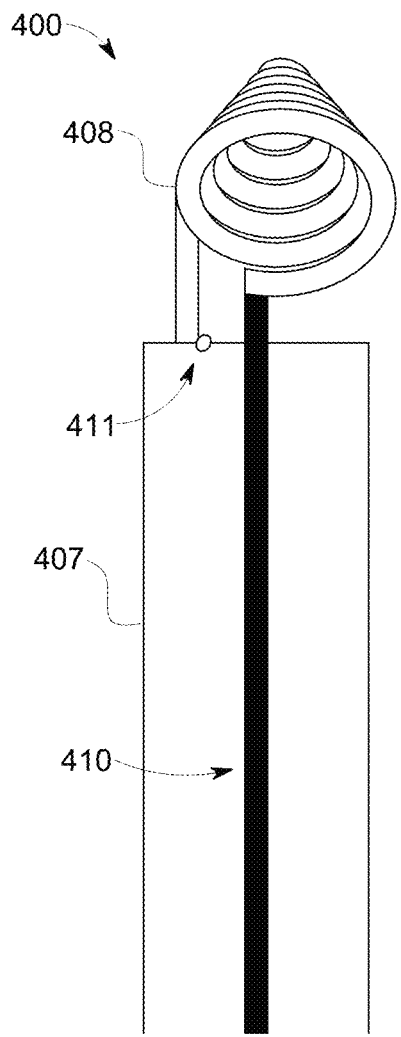
FIGS. 4A and 4B are schematic representations of two configurations of an embodiment of an endovascular probe system in accordance with the disclosed subject matter.
Figure 4B:
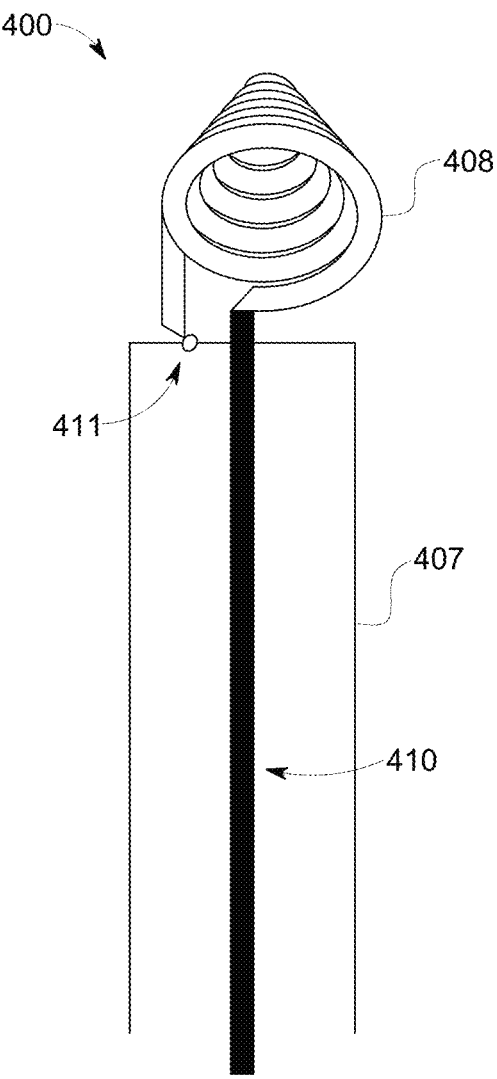

Another embodiment of the probe tip 400 according to the present disclosure is shown in FIG. 4. In this embodiment, the active loop, 408, is mounted on a switch, such as a hinge, latching hinge, bistable mechanism, or any other suitable type of switch, 411. The base of the active loop, 408, contacts and is in electrical communication with the base of the antenna, 407. The probe further comprises a non-conducting mechanical pull wire, which may comprise any suitable MR-compatible material, 410. The pull wire may be fed through the antenna, 407, and attached to a location on the tracking loop, 408. When the pull wire is actuated, the tracking loop, 408, lifts off of the base of the antenna, 407, and terminates electrical contact between 408 and 407. This 'off' state can be seen in FIG. 4B.

Figure 5A:
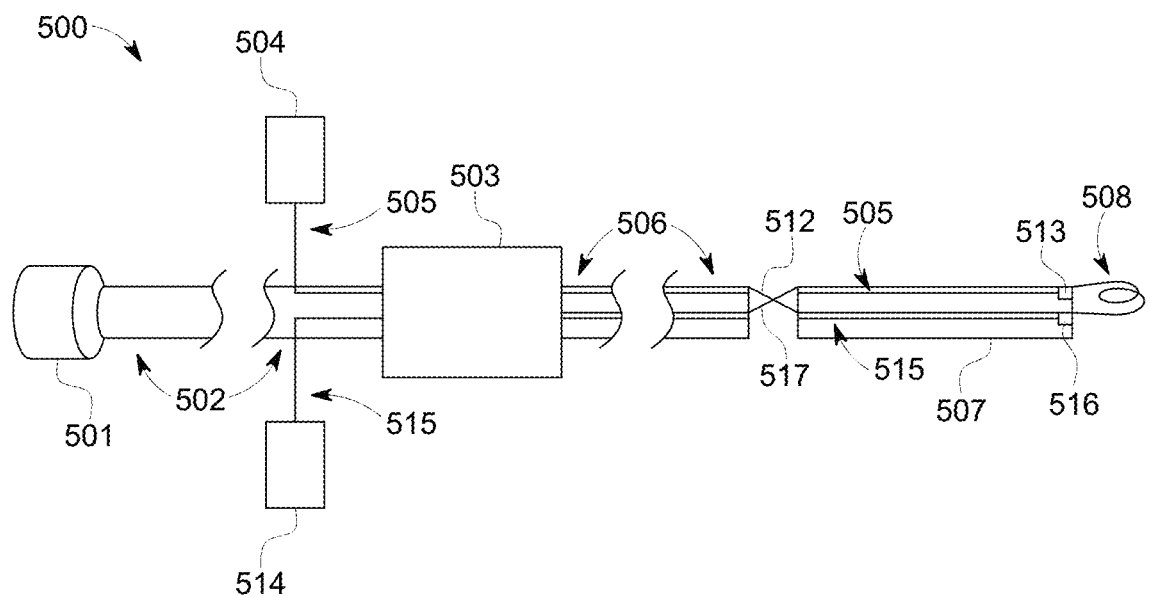
FIGS. 5A-5D are static representations of various configurations of an embodiment of an endovascular probe system in accordance with the disclosed subject matter.

An overview of another embodiment of the device 500 can be seen in FIG. 5A. What distinguishes this embodiment from the aforementioned embodiments is the use of 2 photoactive switches, as well as the use of a different antenna design. In the embodiment shown in FIG. 5A, a bnc connector, 501, connects with the scanner, and its other side is connected to a coaxial cable, 502. The coaxial cable, 502, enters a tuning/matching/decoupling box, 503. On the other side of 503, another coaxial cable, 506, is connected. The inner conductor, 517, of 506, is routed (e.g., soldered) to the outer conductor of another cable, 507. The outer conductor, 512, of 506, is routed (e.g., soldered) to the inner conductor of 507. The cable, 507, may be a coaxial cable with an inner and outer conductor, without any insulation covering the outer conductor (or may comprise a thin layer of insulation, such as silicon). It is important to note that 507 may be any manufactured cable that satisfies the requirements of a clinical-grade device, such as mechanical maneuverability and compliance. Two lasers or illuminating sources, 504 and 514, are connected to separate optical fibers, 505 and 515, respectively. FIG. 5A shows 505 and 515 entering 502, before 503. However, the optical fibers may enter the probe at any suitable location, for example proximal to 503 or distal to 503. In the depicted embodiment, the optical fibers, 505 and 515, are fed through 503, and through non-conducting regions of 506 and 507. The optical fibers, 505 and 515, are incident on separate switchable couplings comprising photoactive materials, 513 and 516, respectively. The photoactive coupling of this embodiment, FIG. 5, may comprise the same materials as are suitable for the coupling described for FIG. 2 and FIG. 3. However, it will be appreciated that the various embodiments of mechanical, photoactive, or thermally active switches described in the remainder of the application may be also used in the embodiment of FIG. 5, and that the first coupling need not be of the same type of the second coupling. For example, one or both sides of loop 508 may be coupled to the remainder of the probe by a mechanical switch.

Figure 5B:
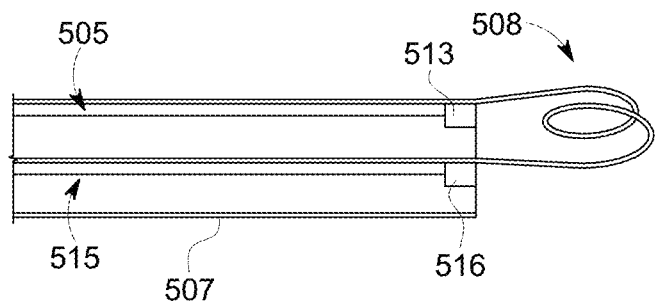

Close up views of the distal tip of the probe are shown in FIGS. 5B, C, and D, which depict different switch configurations. In FIG. 5B, both switchable couplings are in a contracted state, and the tracking loop is in electrical communication with 517, the outer conductor, and 512, the inner conductor, of cable 507. This configuration may be used in an active tracking mode during navigation, and the probe would not be tuned to the operating frequency or impedance matched.

Figure 5C:
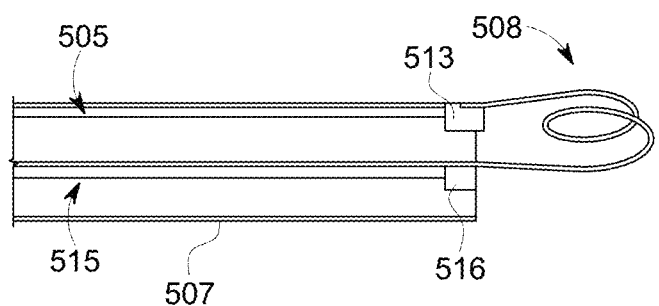

In FIG. 5C, only the switchable coupling including the photoactive material 513, is actuated. The photoactive material 513 is thus in an expanded state, with the first end of 508 displaced away from 517, and thus, electrical contact between 508 and 517 is terminated. The probe may be used as a receiver for high-resolution imaging in this configuration. The probe is constructed so that the act of removing electrical contact from the first end of 508 would leave the probe tuned to the resonant frequency and impedance matched (typically 50 ohm). This configuration would be optimal for using the tuned/matched loopless antenna in receive mode for high-resolution imaging. The outer conductor, 517, is effectively a loopless antenna in this configuration.

Figure 5D:
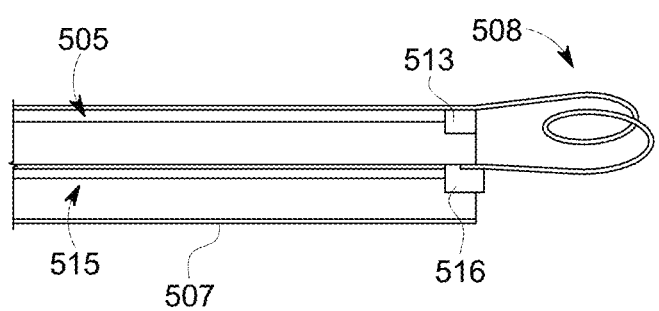

In FIG. 5D, only the switchable coupling including the photoactive material 515, is actuated. The photoactive material 515 is thus in an expanded state, which lifts the second end of 508 away from 512, terminating electrical contact between 508 and 512. We should note that the entire length of 508, from its first end up until its second end, is still in electrical contact with 517. This configuration is useful, for example, to ablate tissue. Ablation is achieved in this configuration by electromagnetic coupling of 508 with an external coil, for example the external coil of a magnetic resonance imaging device. Providing ablation in this manner is particularly advantageous, because delivery of ablation therapy via endovascular access allows greater precision of treatment, and continuous visualization of the anatomy using localized endovascular MRI as described herein allows for careful monitoring of the thermal dose. In this configuration, the probe is tuned to the operating frequency of the external coil, as well as being impedance matched. This is because the active loop, 508, from its first end to its second end, is small in proportion to the effective length of the antenna, so that the resonant frequency and impedance of the probe are minimally altered. This will allow the tracking loop to create a large electric field for ablation of tissue. Ablation may be delivered rapidly (within seconds or minutes) and imaging sequences can be employed after or between ablation sequences to monitor the thermal dose provided. Other open circuit configurations, such as those for FIGS. 2-4, may have tracking loops which significantly alter the resonant frequency and impedance matching of the loopless antenna.

Figure 6A:
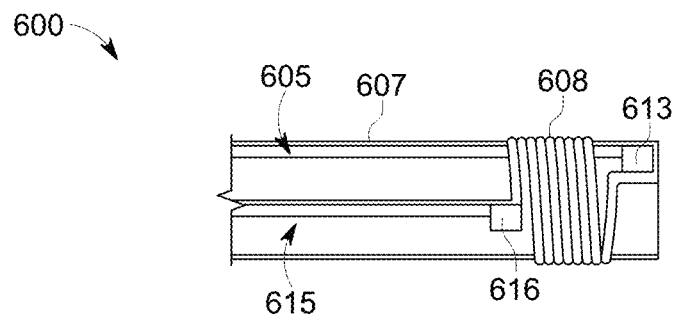
FIGS. 6A-6C are static representations of various configurations of an embodiment of an endovascular probe system in accordance with the disclosed subject matter.
Figure 6B:
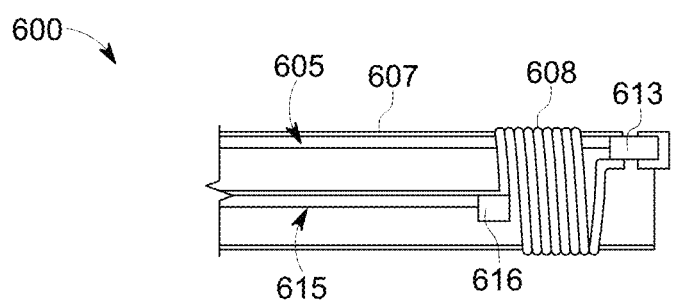
Figure 6C:
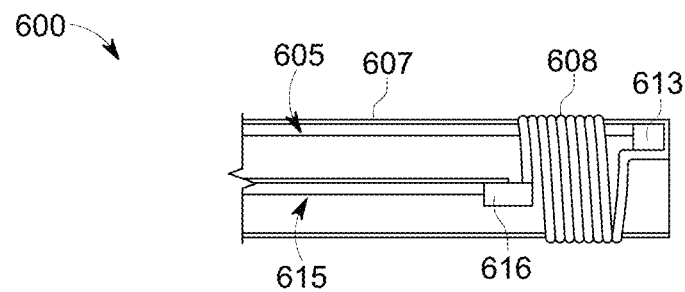

The probe tip 600 of FIG. 6 is very similar to that of FIG. 5. The main difference with FIG. 6 is that the tracking loop, 608, is wrapped in a solenoid around the distal tip of the antenna, 607. There are optical fibers, 605 and 615, incident on separate switchable couplings comprising photoactive materials, 613 and 616, respectively. The photoactive coupling of this embodiment, FIG. 6, may comprise the same materials as are suitable for the coupling described for FIG. 2 and FIG. 3. However, it will be appreciated that the various embodiments of mechanical, photoactive, or thermally active switches described in the remainder of the application may be also used in the embodiment of FIG. 6, and that the first coupling need not be of the same type of the second coupling. The different configurations, FIG. 6A, FIG. 6B, and FIG. 6C, correspond with FIG. 5B, FIG. 5C, and FIG. 5D, respectively.

In a further embodiment of the present invention, one or more long conductive leads may be routed through the center of the antenna and used for direct actuation of a switch. The conductive leads may be connected to an electrically actuated switch, which toggles the tracking loop 'on' and 'off'. An example of an electrothermally activated switch is an electrothermally activated switch for a microvalve comprising paraffin based materials. However, additional electrical leads further complicate the heating problems with endovascular instruments under MRI, as well as exacerbating the spatial challenges of operating within blood vessels.

Additionally, the embodiments of the present invention depicted thus far have described ways of providing a localizing signal for the loopless dipole antenna and an additional design which also resembles a guidewire, which can be turned 'on' and 'off'. Other RF probes may benefit from this switching mechanism, and the present invention is not meant to limit its use to the specific probe designs, (e.g., loopless antenna and coil designs) described herein.

The probes of the present disclosure may be used in a number of methods, as described herein.

In certain embodiments, during a percutaneous procedure, vascular access is obtained through the femoral artery. Other routes can be accessed through the vasculature of the arms, such as the radial artery, and neck. Once a probe as described herein enters the vasculature, it is then guided to the vasculature of interest. This is achieved by using the body coil of the scanner (or other external surface coils) to transmit pulses and the probe with the tracking loop receives the signals. It is not necessary during the active tracking procedure for the probe to be tuned to the Larmor frequency of precessing protons or to be impedance matched to 50 ohms. In another method, the endovascular probe can operate in both transmit and receive modes for active tracking.

According to these embodiments, the probe receives signals and the tracking loop acts as a point detector. By applying readout gradients sequentially in the x, y, and z directions, each following a non-selective (or weakly selective) RF excitation pulse, with the tracking loop receiving the signal, the distal tip of the probe where the tracking loop resides is localized in 3D space. It is an advantage of the present disclosure that the probe may be localized without taking an image. The tracking loop provides a sharp peak in the frequency spectrum of each 1D Fourier projection (x,y, z), and thus gives its 3D coordinates within the scanner. This localization information can be obtained at rates of up to 50 frames per second. In this configuration, the rate-limiting step of the procedure is not the acquisition of localization information, but is the acquisition of background reference images to visualize anatomy around the probe. Each background reference image is acquired with the external or surface coil in receive mode. During acquisition of background reference images, and specifically during RF transmit, the endovascular probe should be entirely decoupled from the surface or body coils. Otherwise, the probe would strongly couple with the body/external coil (mutual inductance) and cause tissue burns during certain pulse sequences. This decoupling is achieved with an additional capacitor and diode (the decoupling component of the tuning/matching/decoupling box). Actually, in the embodiments described, the probe would not be tuned/matched during this part of the procedure, so the decoupling can be seen as a second safety measure to prevent heating. The 3D position of the tracking loop signal provides the scan plan update, and its position in 2D coordinates can be overlaid on the background reference image with a visual marker. This procedure can be done repeatedly at from 1 to 10 frames, or more, per second depending on how much detail is desired in the background reference.

Once the probe has been maneuvered to the desired position within the vasculature, it is switched to an imaging configuration and the antenna portion of the probe is used in receive mode for high-resolution imaging. First, surface or body coils provide RF transmit, and during this transmission, the probe is decoupled. The endovascular probe is tuned and matched during receive mode for MRI signal reception. Alternatively, the probe may be tuned/matched and used to transmit and receive. In either case, the very small tracking loop may cause heating concerns when in an open circuit configuration, since it is tiny and losses are high at that location. The switching mechanism disclosed herein removes the tracking loop from the circuit during receive mode with the loopless antenna for high-resolution imaging. The loop will not couple to the rest of the antenna because its resonant frequency is far from the operating frequency of the scanner (and antenna), and thus, there is minimal voltage (no heating hazards) at the loop. The tracking loop does not serve to image at the distal tip. Rather, it is used during the active tracking procedure to give the precise location of the distal antenna tip and is then disengaged during high-resolution imaging when RF power is greatest. The tracking loop can then be re-engaged for delivery of ablation. The probe would be tuned/matched in this configuration and ablation can be performed by inducing currents in the probe from pulse sequences of the scanner or by connecting an external ablation generator.

Places where conductors cross each other are additional "hot spots". In the configurations of FIG. 5B and FIG. 6A, crossing of conductors occurs at the junction of coaxial cables, or other clinical grade cables, and if these configurations were tuned during imaging with the probe as a receiver or during active tracking guidance, they may cause concern for tissue heating. Even if heating from the tracking loop or coax junction when the probe is in receive mode is minimal for all pulse sequences, the switch allows for easy control over all of the different modes—imaging, tracking, and ablation. Beyond heating considerations, there is an interplay between the different probe configurations as well as the different procedural steps. Keeping the probe detuned during active tracking and guidance allows for background reference images to be obtained with external coils without excessive signal gain from the proximal imaging portion of the antenna, which could distort the background reference images. Also, if the probe was tuned and matched during active tracking guidance, the large amount of signal at the antenna/coax junction could cause misregistration of the position of the tracking loop to the junction, especially if tortuous vasculature is navigated, where the probe tip would be bent closer to the junction. Switching the tracking coil 'off' allows the probe to be tuned and matched when it is used to image deep vascular anatomy. This will be appreciated after considering FIG. 9.

EXEMPLIFICATION

Various embodiments of the present disclosure now being generally described, it will be more readily understood by reference to the following examples which are included merely for purposes of illustration of certain aspects and embodiments of the present invention, and are not intended to limit the invention.

Example 1

RF Properties of Exemplary Probe Tip Configurations

Finite element method (FEM) simulations of one possible ablation loop configuration were conducted, similar to the configuration shown in FIG. 5D. FEM simulation models (COMSOL) were built with a domain with the dielectric properties of blood/saline, to include 'first order' physiological sample loading conditions. The switch mechanism was not included in the geometry because only the RF performance of the coil was assessed. The antenna was modeled as the stripped inner conductor of a coaxial transmission line, with an antenna diameter of 2 mm. Only a short segment of the transmission line was included in the simulations (4 mm) with a ground plane situated at the proximal end of the antenna. All conducting components were modeled as perfect electric conductors. The transmission line port was excited with a nominal 1V AC. The port impedance was adjusted to match the antenna impedance and simulations of the reflection (S11) coefficient were run to make sure the probe resonated at the operating frequency. The antenna measures a quarter wavelength (4.7 cm), as determined by the Larmor frequency at 3T and sample loading conditions. The local Specific Absorption Rate (SAR) at the tip of the small tracking/ablation loop was also simulated, given by:

$$SAR = \sigma \frac{E^2}{\rho}$$

where E is the electric field norm, σ is the conductivity of the medium, and ρ is the density of the medium. The model numerically solves (approximates) the vector-Helmholtz equation at 128 MHz within the entire, spherical simulation domain. It will be realized that certain simplifying assumptions were made when constructing this model. Some assumptions reduce the computational load of the simulations, and others are based on the data obtained from the simulations and subsequent analysis of that data. For example, we are not concerned with simulating the absolute SNR of the probe, and are more interested in showing relative differences that arise when altering a single parameter.

Figure 7:
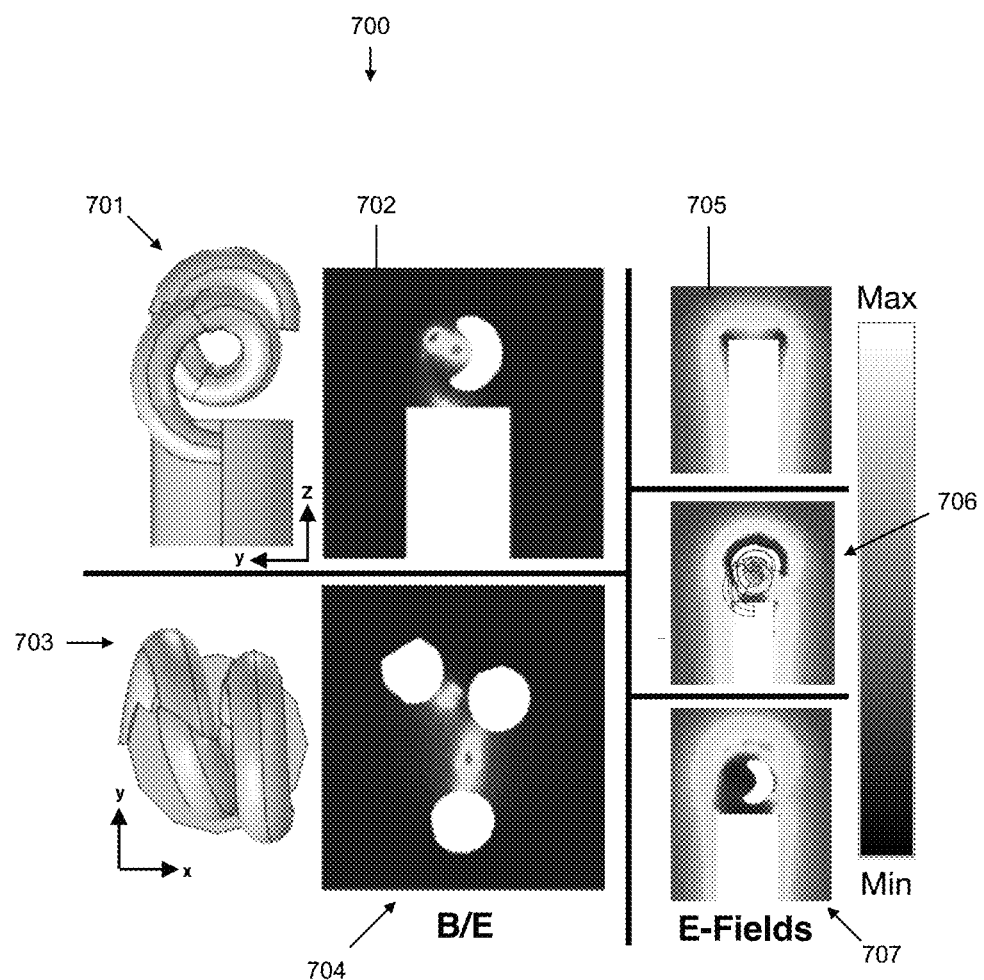
FIGS. 7 and 8 show the results of finite element method (FEM) simulations of one possible tracking/ablation loop configuration in accordance with the disclosed subject matter.

In FIG. 7, according to visualization 700, The B/E metric (which is proportional to SNR), where B is the magnetic field norm and E is the electric field norm, is mapped for two different views (702, 704), giving a visual of the localized signal gain in the axis of the loop. The signal gain, however, is contained within a tiny volume. The 3D CAD renderings of the simulated ablation/tracking mechanism can be seen in 701 and 703. As shown, the ablation/tracking loop contains less than 2 turns with its second end left unconnected and was found to produce a weak tracking signal. This loop containing roughly two turns can be used for active tracking if it is in the configuration of FIG. 5B. Nonetheless, the simulations are not inaccurate, and they serve an important purpose: mapping the fields around the probe and calculating other important parameters such as S11 and power deposition. The electric fields are shown (705, 706, 707) for the cases of a bare antenna (705), and the antenna with a tracking loop at the distal-most section (706) and at the center of the loop (707) where the electric void allows for signal gain.

Figure 8:
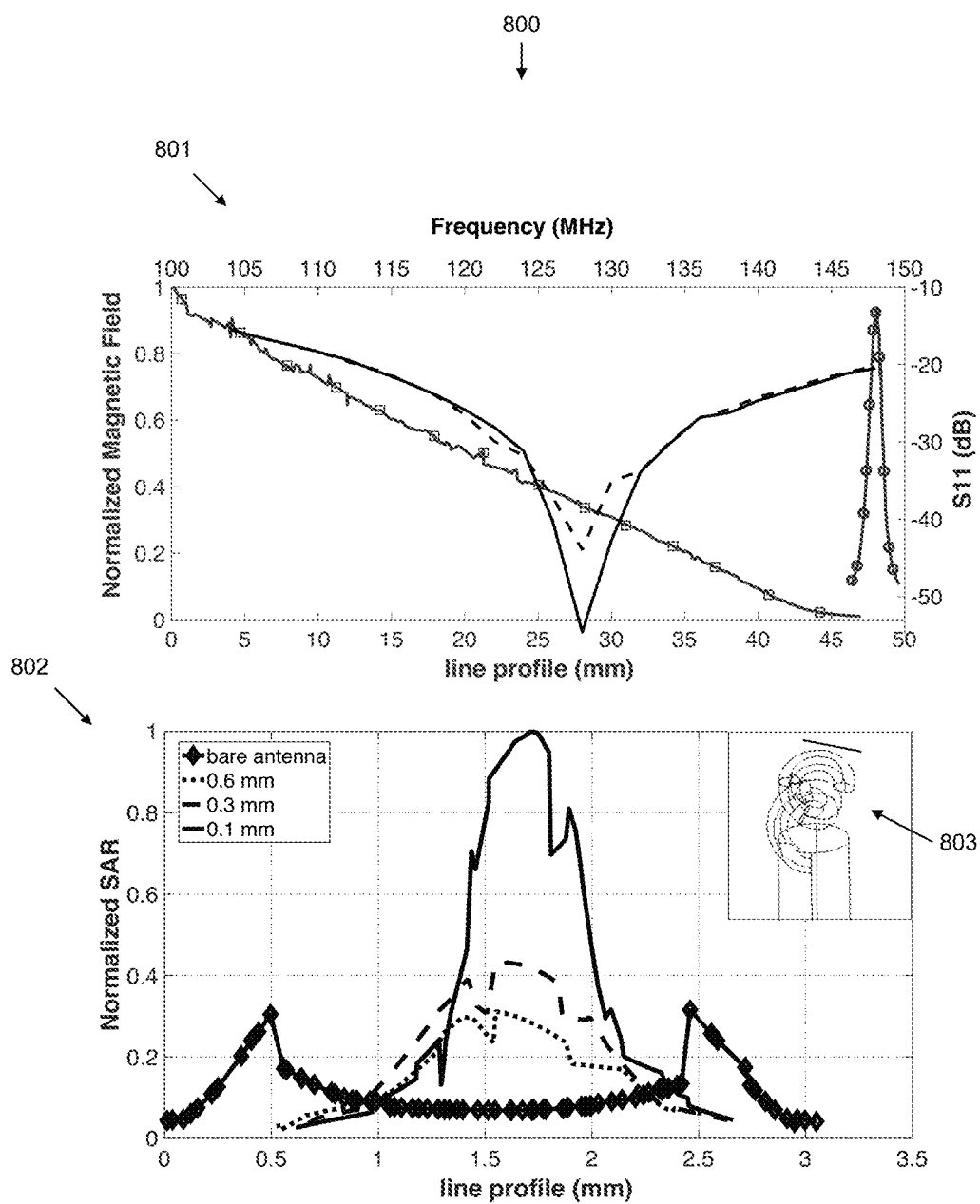

In FIG. 8, according to visualization 800, simulated reflection coefficients (S11), 801, are shown for the tuned and matched bare antenna (black line) and the antenna with the added ablation/tracking loop (black dashes), using the top and right axes. The normalized transverse magnetic field is plotted for two cases at a distance of 2 mm away from the surface of the antenna (gray profile with squares), and through the center axis of the inductive loop (gray line profile on far right with circles) (bottom and left axes). The normalized SAR can be seen (802) for the tip of the bare antenna and ablation/tracking loops containing different wire diameters (0.6 mm, 0.3 mm, 0.1 mm). The inset (803) shows the chosen location of the line profile for the ablation/tracking loop, which is 0.1 mm away from the surface of the loop at the closest position for each case with different wire diameters. At this frequency of 128 MHz, the SAR at the tip of the 0.1 mm diameter wire is roughly 3.2 times greater than the max SAR at the tip of a bare antenna. This is an expected result-small diameter conductors with tortuous bends are lossy.

Figure 9:
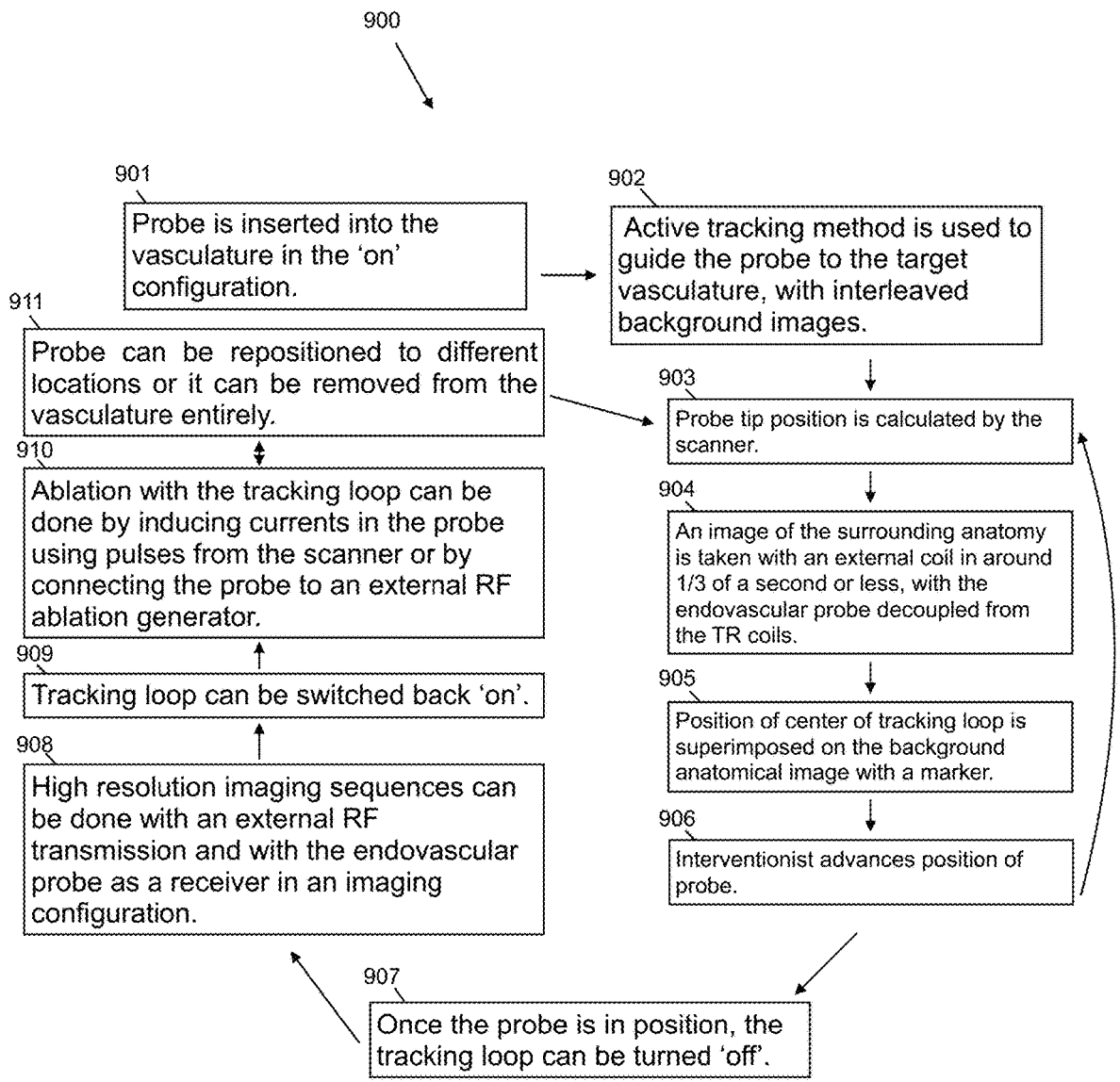
FIG. 9 is a flow diagram of an embodiment of a method in accordance with the disclosed subject matter.

A flow diagram of one possible method 900 is shown in FIG. 9. First, the probe is inserted into the vasculature, 901, with the tracking loop in electrical communication with the conductor(s) of the antenna. A tracking and imaging method, 902, is used to guide the probe to the target vasculature. If the probe used is the embodiment of FIG. 5, then the probe would be in the configuration of FIG. 5B. First, the tip position is calculated by the scanner, 903. Then, an image of the surrounding anatomy is produced in 1/3 of a second or less, 904. The position of the tracking loop is superimposed on the anatomical image, 905. These steps are done at 1-10 frames per second, and the interventionist navigates the position of the probe throughout the vasculature, 906. When the probe reaches a target location, the tracking loop can then be disengaged by actuation of the switching mechanism, 907. If the probe used is the embodiment of FIG. 5, then the probe would be in the configuration of FIG. 5C. High-resolution imaging sequences can be obtained with an external RF transmission and with the endovascular probe as a receiver, 908. Or, the probe can be used to transmit and receive. Once imaging is finished, the tracking loop can be re-engaged, 909. If the probe used is the embodiment of FIG. 5, its configuration would be as depicted in FIG. 5D. Ablation therapy can then be delivered, with the tracking loop, or antenna, as a precision source for therapy, 910. Ablation can be delivered by inducing currents in the probe from RF pulses of the scanner (Hue, Yik-Kiong. et al. *IEEE transactions on medical imaging* 37.2 (2018); 417-427). Alternatively, an ablation generator can be hooked up to the proximal portion of the probe. Once ablation is discontinued, the probe can be repositioned to other locations or it can be removed from the vasculature of the patient, 911.

When actuating the switchable coupling for the various configurations, it may be necessary to apply a short duration of relatively high power irradiation to quickly change the shape of the photoactive material. This will allow the change of shape to occur in 1 second or less. To maintain this altered shape of the photomechanical material, it may also be necessary to ramp down the power of the illuminating source such that the material reaches a steady state at the actuation temperature. This may be needed to prevent a continued rise in temperature of the material, which could cause ambient heating of tissue, or damage the material to an extent that prevents repeated actuation (Wani, Owies M., et al. *Nature communications* 8 (2017): 15546). Depending on the nature of the photoactive material, it may be necessary to illuminate it with one particular wavelength of light to induce shape change, and it may be necessary to illuminate it with another wavelength of light in order to reverse the shape change.

EQUIVALENTS

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

I claim:

1. An endovascular probe, comprising:
   a loopless antenna comprising a conductor;
   a tracking coil with a first end and a second end; and
   a switchable coupling coupled to the conductor and the first end of the tracking coil, the switchable coupling disposed at a distal tip of the endovascular probe, wherein:
      when the switchable coupling is in a first state, the conductor of the loopless antenna is in electrical communication with the first end of the tracking coil and the endovascular probe is in a tracking probe mode; and
      when the switchable coupling is in a second state, the conductor of the loopless antenna is not in electrical communication with the first end of the tracking coil and the endovascular probe is in an imaging probe mode,
      wherein each of the tracking coil, the switchable coupling and the loopless antenna use a shared transmission cable including the conductor.

2. The endovascular probe of claim 1, wherein the switchable coupling comprises:
   a photoresponsive material mechanically coupled to the conductor and the tracking coil; and
   an optical fiber in optical communication with a switching material.

3. The endovascular probe of claim 2, further comprising a light source in optical communication with the optical fiber.

4. The endovascular probe of claim 2, wherein the switchable coupling further comprises a membrane enclosing the switching material.

5. The endovascular probe of claim 2, wherein the photoresponsive material has a positive coefficient of thermal expansion and further wherein:
   when the photoresponsive material is at a first temperature, the switchable coupling is in the first state; and
   when the switching material is at a second temperature that is higher than the first temperature, the switchable coupling is in the second state.

6. The endovascular probe of claim 2, wherein the photoresponsive material has a negative coefficient of thermal expansion and further wherein:
   when the switching material is at a first temperature, the switchable coupling is in the second state; and
   when the switching material is at a second temperature that is higher than the first temperature, the switchable coupling is in the first state.

7. The endovascular probe of claim 1, further comprising:
   a switching device mechanically coupled to the tracking coil; and
   a wire mechanically coupled to the switching device.

8. The endovascular probe of claim 7, wherein the switching device comprises a hinge.

9. The endovascular probe of claim 8, wherein the hinge is bistable.

10. The endovascular probe of claim 1, further comprising a second conductor; wherein the second conductor is in electrical communication with the second end of the tracking coil.

11. The endovascular probe of claim 1, further comprising a second conductor; wherein the endovascular probe further comprises a second switchable coupling mechanically coupled to the second conductor and the second end of the tracking coil.

12. The endovascular probe of claim 11, wherein the second switchable coupling further comprises:
    a second photoresponsive material mechanically coupled to the second conductor and the second end of the tracking coil; and
    a second optical fiber in optical communication with the switching material.

13. The endovascular probe of claim 12, further comprising a second light source in optical communication with the second optical fiber.

14. The endovascular probe of claim 12, wherein the switchable coupling further comprises a membrane enclosing the switching material.

15. The endovascular probe of claim 1, wherein the first end of the tracking coil is a distal end of the tracking coil.

16. The endovascular probe of claim 1, wherein the shared transmission cable is a coaxial cable.

17. A method of operating an intravascular probe, comprising:
    providing an endovascular probe comprising:
       a loopless antenna comprising a conductor;
       a tracking coil with a first end and a second end; and
       a switchable coupling coupled to the conductor and the first end of the tracking coil, the switchable coupling disposed at a distal tip of the endovascular probe, wherein:
          when the switchable coupling is in a first state, the conductor of the loopless antenna is in electrical communication with the first end of the tracking coil and the endovascular probe is in a tracking probe mode; and
          when the switchable coupling is in a second state, the conductor of the loopless antenna is not in electrical communication with the first end of the tracking coil and the endovascular probe is in an imaging probe mode, wherein each of the tracking coil, the switchable coupling and the loopless antenna use a shared transmission cable including the conductor;

inserting the endovascular probe into a blood vessel;

tracking the position of the tip of the endovascular probe in the blood vessel; and collecting an image of the anatomy surrounding the endovascular probe.

18. The method of claim 17, wherein tracking the position of the tip of the endovascular probe comprises placing the endovascular probe in the first state and applying a tracking pulse sequence.

19. The method of claim 17, wherein collecting an image comprises placing the endovascular probe in the second state and applying an imaging pulse sequence.

20. The method of claim 17, further comprising placing the endovascular probe in an ablation state and applying an ablation pulse sequence.

* * * * *